United States Patent [19]

Spitzer

[11] Patent Number: 4,537,889

[45] Date of Patent: Aug. 27, 1985

[54] INOTROPIC AGENTS

[75] Inventor: Wayne A. Spitzer, Indianapolis, Ind.

[73] Assignee: Eli Lilly and Company, Indianapolis, Ind.

[21] Appl. No.: 606,806

[22] Filed: May 3, 1984

Related U.S. Application Data

[62] Division of Ser. No. 453,565, Dec. 27, 1982, abandoned.

[51] Int. Cl.$^3$ .................... C07D 487/04; A61K 31/53
[52] U.S. Cl. .................... 514/243; 544/184; 514/245; 514/246
[58] Field of Search .................... 544/184; 424/249

[56] References Cited

U.S. PATENT DOCUMENTS

| | | | |
|---|---|---|---|
| 2,837,520 | 6/1958 | Fusco et al. | 544/184 |
| 3,719,677 | 3/1973 | Loev | 544/184 |
| 3,978,071 | 8/1976 | Nakanishi et al. | 260/295 K |
| 3,985,891 | 10/1976 | Kutter et al. | 424/263 |
| 4,107,308 | 8/1978 | Paul et al. | 544/184 |
| 4,151,210 | 4/1979 | Weis | 260/607 AR |
| 4,166,851 | 9/1979 | Baldwin et al. | 424/248.55 |
| 4,233,301 | 11/1980 | Baldwin et al. | 424/250 |
| 4,299,834 | 11/1981 | Austel et al. | 424/253 |
| 4,324,628 | 4/1982 | Avar et al. | 204/159.24 |
| 4,327,100 | 4/1982 | Austel et al. | 424/256 |
| 4,336,257 | 6/1982 | Baldwin | 424/256 |
| 4,353,909 | 10/1982 | Diederen et al. | 424/256 |

FOREIGN PATENT DOCUMENTS

| | | | |
|---|---|---|---|
| 61380 | 3/1981 | European Pat. Off. | |
| 52016 | 5/1982 | European Pat. Off. | |
| 1026321 | 3/1958 | Fed. Rep. of Germany | |
| 2510576 | 7/1981 | France | |
| 1092526 | 11/1967 | United Kingdom | 544/184 |
| 478006 | 7/1975 | U.S.S.R. | 544/184 |

OTHER PUBLICATIONS

Saraswathi et al., Indian Journal of Chemistry, vol. 15B, pp. 607–610, (Jul. 1977).
Derwent Abstract of German OLS DE 3,044,497.
*Annual Reports in Medicinal Chemistry,* 16, 88 (1981).
*Annual Reports in Medicinal Chemistry,* 17, 93 (1982).
Derwent D/39 70803, summarizing Japanese Patent J5 6100-783, Aug. 1981.
Derwent E/37 76695, abstracting Belgian Pat. No. 892,339, Sep. 1982.

*Primary Examiner*—John M. Ford
*Attorney, Agent, or Firm*—Charles W. Ashbrook; Arthur R. Whale

[57] ABSTRACT

This invention provides for certain phenyl-substituted imidazo compounds, their pharmaceutical formulations, and their use as positive inotropic agents and vasodilators.

10 Claims, No Drawings

INOTROPIC AGENTS

This application is a division of application Ser. No. 453,565, filed Dec. 27, 1982, now abandoned.

BACKGROUND OF THE INVENTION

The cardiac glycosides and the sympathomimetic amines are the principal inotropic agents used in the management of congestive heart failure. Although the cardiac glycosides, especially digitalis, are among the most frequently prescribed drugs, they have numerous liabilities such as a low therapeutic index and erratic absorption, and are associated with life-threatening arrhythmias and deleterious drug-drug interactions. In addition, many patients either do not respond, or become refractory to these agents. The sympathomimetic amines, such as dopamine and epinephrine, have limited utility due to positive chronotropic effects, arrhythmogenic properties, and oral ineffectiveness.

More recently, new classes of inotropic agents have been found. Among these, certain 2-phenylimidazo[4,5-b]pyridines (U.S. Pat. Nos. 3,985,891 and 4,327,100) have been shown to possess inotropic and anticoagulant activity. U.S. Pat. Nos. 4,299,834 and 4,353,909, and German Patent DE No. 3,044,497, described in Derwent E/26 52573, describe similarly substituted purine and 6-hydroxy-imidazo[4,5-b]pyridine derivatives.

Imidazo[1,2-a]pyridines substituted at the 2-position with carbostyril derivatives are described in European Patent Application No. 52,016. The compounds are said to be useful as cardiotonic agents. The circulatory and respiratory effects of 2-(2-pyridyl)-[1,2,4]-triazolo[1,5-a]pyridine is described in Derwent Abstract D/39 70803 (abstracting Japanese Patent J5 6100783).

The present invention provides for a series of phenyl-imidazole compounds, their formulations, and their use as orally effective positive inotropic agents which have minimal effects on blood pressure and heart rate. The compounds also possess vasodilitation activity.

SUMMARY OF THE INVENTION

This invention provides for pharmaceutically useful compounds having the formula

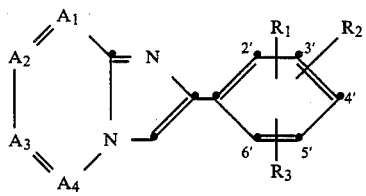

and their pharmaceutically acceptable salts, wherein one or two of $A_1$, $A_2$, $A_3$, and $A_4$ is N, and the remaining $A_1$, $A_2$, $A_3$, and $A_4$ are CH, with the proviso that if $A_4$ is N, one of $A_1$, $A_2$, and $A_3$ is also N; and each of $R_1$, $R_2$, and $R_3$ is independently hydrogen, $C_1$-$C_4$ alkyl, $C_1$-$C_4$ alkoxy, allyloxy, benzyloxy, ($C_1$-$C_4$ alkyl)thio, ($C_1$-$C_4$ alkyl)sulfinyl, ($C_1$-$C_4$ alkyl)sulfonyl, hydroxy, halo, cyano, nitro, amino, mono- or di-($C_1$-$C_4$ alkyl)amino, trifluoromethyl, or Z-Q-substituted $C_1$-$C_4$ alkoxy, wherein Q is oxygen, sulfur, sulfinyl, sulfonyl, or a bond, and Z is $C_1$-$C_4$ alkyl, phenyl or phenyl substituted with halo, $C_1$-$C_4$ alkyl, $C_1$-$C_4$ alkoxy, hydroxy, nitro, amino, $C_1$-$C_4$ alkylthio, $C_1$-$C_4$ alkylsulfinyl, or $C_1$-$C_4$ alkylsulfonyl.

In addition to the compounds of formula I, this invention also provides a method of treating a warm-blooded mammal, including a human, suffering from or susceptible to the conditions of hypertension or heart failure, which comprises administering to said mammal a therapeutically effective amount of a compound of formula I.

According to a further aspect of the present invention there is provided a pharmaceutical formulation which comprises as active ingredient a therapeutically effective amount of a compound of Formula I as defined above, associated with a pharmaceutically acceptable carrier therefor.

This invention also provides certain intermediates necessary to prepare the preferred compounds of this invention.

DETAILED DESCRIPTION AND PREFERRED EMBODIMENT

The compounds of Formula I may be given common chemical names depending upon the ring-system arrangement of $A_1$, $A_2$, $A_3$ and $A_4$. The nine possibilities are drawn below:

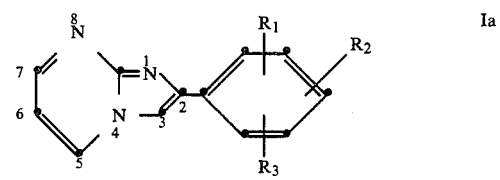

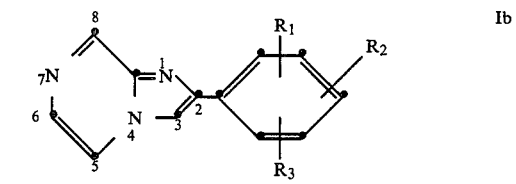

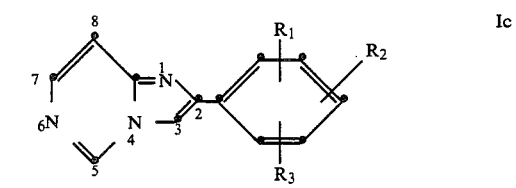

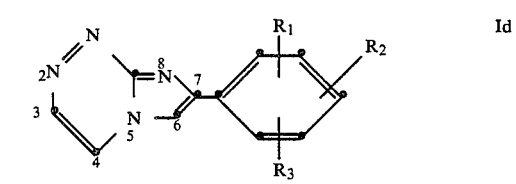

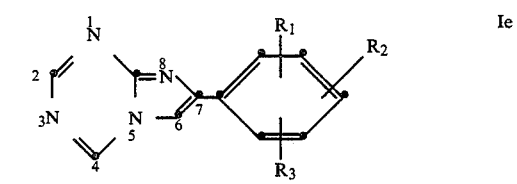

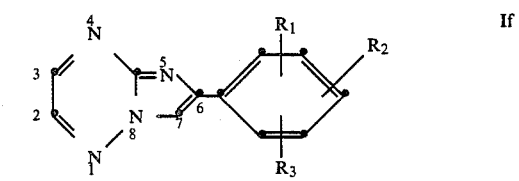

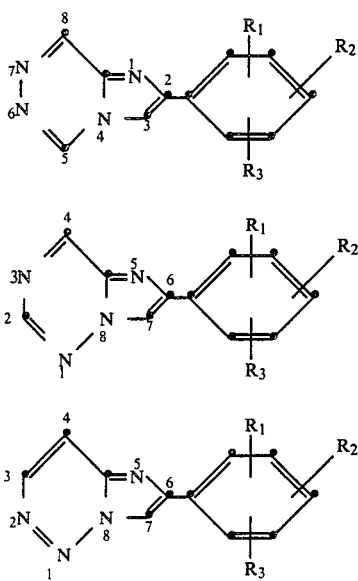

These ring systems can be named in the following manner: Ia, 2-phenylimidazo[1,2-a]pyrimidine; Ib, 2-phenylimidazo[1,2-a]pyrazine; Ic, 2-phenylimidazo[1,2-c]pyrimidine; Id, 7-phenylimidazo[2,1-c][1,2,4]triazine; Ie, 7-phenylimidazo[1,2-a]-1,3,5-triazine; If, 6-phenylimidazo[1,2-b][1,2,4]triazine; Ig, 2-phenylimidazo[1,2-d][1,2,4]triazine; Ih, 6-phenylimidazo[2,1-f][1,2,4]triazine; Ii, 6-phenylimidazo[1,2-c][1,2,3]triazine. Preferred ring systems are those with three nitrogen atoms in the ring system, i.e., the imidazo-pyrimidines Ia and Ic and imidazo-pyrazine Ib.

A preferred group of compounds are those which have one or two substituents on the phenyl ring especially those selected from $C_1$–$C_4$ alkyl, $C_1$–$C_4$ alkoxy, halogen, ($C_1$–$C_4$ alkyl)thio, ($C_1$–$C_4$ alkyl)sulfinyl, ($C_1$–$C_4$ alkyl)sulfonyl, or Z-Q-substituted $C_1$–$C_4$ alkoxy; and pharmaceutically acceptable salts thereof.

Preferred groups of compounds are those compounds wherein the substituents are at the 3' and 4', and especially the 2' and 4' positions of the phenyl ring.

Especially preferred groups are defined above are those where "$C_1$–$C_4$ alkyl" is methyl, "$C_1$–$C_4$ alkyl sulfinyl" is methylsulfinyl, "$C_1$–$C_4$ alkyl sulfonyl" is methylsulfonyl, and "$C_1$–$C_4$ alkoxy" is methoxy. Preferred Z-Q-substituted $C_1$–$C_4$ alkoxy compounds are those wherein $C_1$–$C_4$ alkoxy is ethoxy or n-propoxy, Q is oxygen, sulfur, sulfinyl, or sulfonyl, and Z is $C_1$–$C_4$ alkyl, phenyl or phenyl substituted with halo, $C_1$–$C_4$ alkoxy, or hydroxy. Compounds substituted at the 2' position of the phenyl ring with $C_1$–$C_4$ alkoxy, especially methoxy, or with the preferred Z-Q-substituted $C_1$–$C_4$ alkoxy substituents, and at the 4'-position of the phenyl ring with $C_1$–$C_4$ alkoxy, $C_1$–$C_4$ alkylsulfinyl, or $C_1$–$C_4$ alkylsulfonyl are particularly preferred, with 2',4'-dimethoxyphenyl, 2'-methoxy-4'-methylsulfinylphenyl, and 2'-methoxy-4'-methylsulfonylphenyl groups being most preferred.

The following definitions refer to the various terms used throughout this disclosure.

The term "halo" refers to fluoro, chloro, bromo, and iodo.

The term "$C_1$–$C_4$ alkyl" refers to the straight and branched aliphatic radicals of one to four carbon atoms including methyl, ethyl, propyl, isopropyl, butyl, isobutyl, sec-butyl, and tert-butyl.

The term "$C_1$–$C_4$ alkoxy" includes the straight and branched aliphatic ether radicals of one to four carbon atoms such as methoxy, ethoxy, propoxy, isopropoxy, butoxy, isobutoxy, sec-butoxy, and tert-butoxy.

The compounds of this invention as represented by Formula I may be prepared by any of several methods known in the art.

A preferred method of preparation consists of the reaction of an amine of the formula II

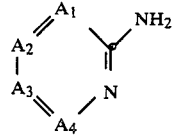

wherein $A_1$, $A_2$, $A_3$ and $A_4$ are as defined above, with an α-haloketone of the formula

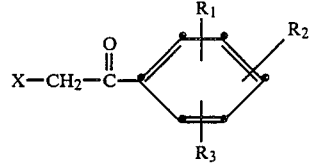

wherein $R_1$, $R_2$, and $R_3$ are as defined above and X is halo, preferably bromo or chloro. The reaction may be performed in the absence of a solvent, but is generally carried out in a suitable non-reactive solvent, such as dimethylformamide, benzene, toluene, xylene, ethylene glycol, pyridine, acetone, and the like. Temperatures in the range of −20° C. to 250° C. may be employed with a preferred range of 20°–60° C.

An alternate procedure to provide the compounds of Formula I consists of the reaction as described above wherein the amine intermediate is similar to II except that one of $A_1$, $A_2$, or $A_3$, which is usually CH adjacent to another of $A_1$, $A_2$, or $A_3$ which is N, is now CX, preferably CCl. This halo-substituted heterocyclic amine (II') may be used in place of II in the reaction with III to provide the corresponding halo-substituted compounds of this invention (referred to as I'). The advantage in using the halo-substituted heterocyclic amine II' is found in the relatively increased reactivity of the amine which provides the intermediates I' in greater yields and purity. The halo intermediates I' are then transformed into the desired compounds I by catalytic hydrogenation, such as reacting I' with hydrogen in an inert solvent in the presence of a catalyst, such as palladium-on-carbon or palladium-on-barium sulfate. An acid scavenger, such as a trialkylamine, may be added to form a salt with the hydrohalide formed as a by-product.

The amine starting materials II and II' are commercially available or may be prepared in the usual manner from available starting materials by the proper sequence of nitrations, reductions, acylations, hydrolyses, halogenations, and aminations. The required α-haloketones of Formula III are either commercially available, are known in the literature, or are prepared by published methods or by methods described herein.

The sulfinyl and sulfonyl derivatives of this invention may be prepared directly by the reaction of the corresponding intermediates III with II, or by oxidation of the corresponding mercapto compounds of Formula I by methods known in the art. One or two equivalents, respectively, of hydrogen peroxide in an alcohol, a peracid, such as meta-chloroperbenzoic acid in methylene chloride, or similar oxidants may be used to effect these transformations.

Certain of the intermediate acetophenone derivatives III are novel and are useful in preparing some of the preferred compounds of Formula I. Accordingly, these compounds, as represented by formula III'

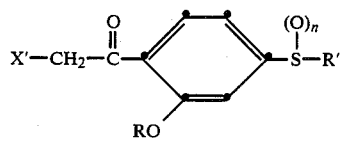

III' where X' is bromo or chloro, each of R and R' is independently $C_1$–$C_4$ alkyl, and n is 0, 1, or 2, are claimed as part of this invention. The compounds of formula III' can be prepared by the following two schemes:

In Scheme I, commercially available 2,4-dihydroxyacetophenone is transformed into the corresponding 2-($C_1$–$C_4$ alkoxy) derivative by first blocking the 4-hydroxy functionality with a group such as benzyl by methods known in the art. The remaining 2-hydroxy functionality is then alkylated with a suitable $C_1$–$C_4$ alkyl halide in the usual manner after which the blocking group is removed. The free phenol is then transformed into the corresponding thiophenol by first forming the thiocarbamic acid ester, rearranging by heating to form the carbamoyl mercapto intermediate, and deblocking by basic hydrolysis. The thiophenol is then alkylated with the appropriate R'-halide in the usual way and the acetophenone is then halogenated either directly by using elemental bromine or chlorine or indirectly by treating an intermediate silyl derivative with N-bromo- or N-chloro-succinimide. All the above reactions and transformations are known to those skilled in the art. The resulting thioether derivative may be then coupled with II as described above, or first converted to the corresponding sulfoxide or sulfone derivative by the usual methods as described previously.

An alternate procedure for preparing the compounds of Formula III' is summarized in Scheme II.

Scheme I

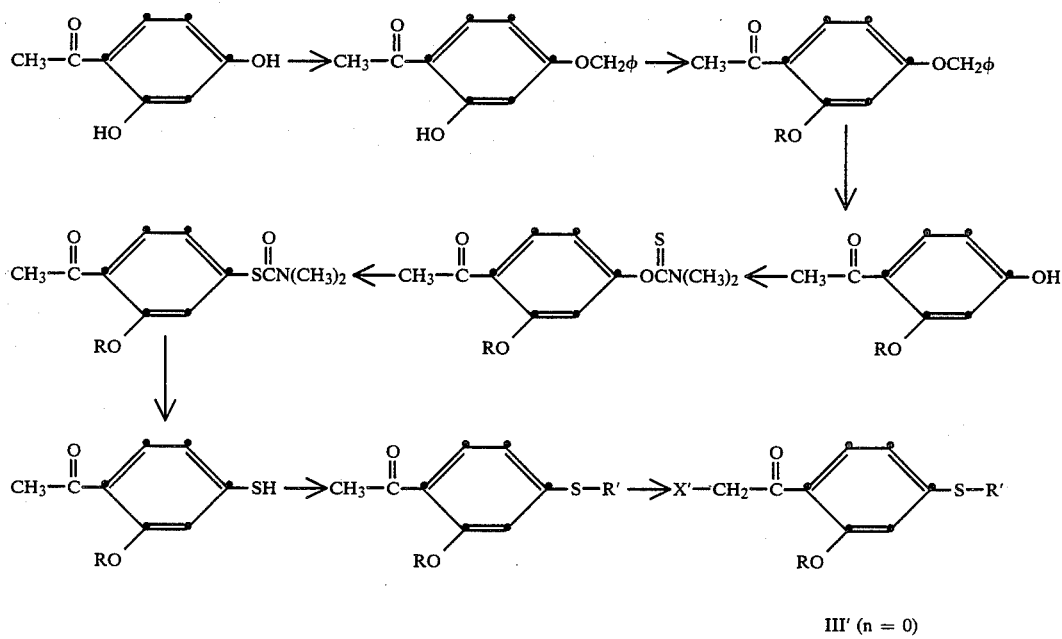

III' (n = 0)

Scheme II

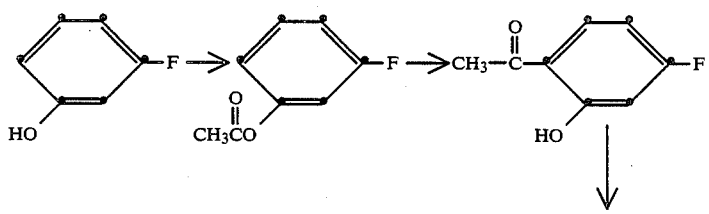

Scheme II

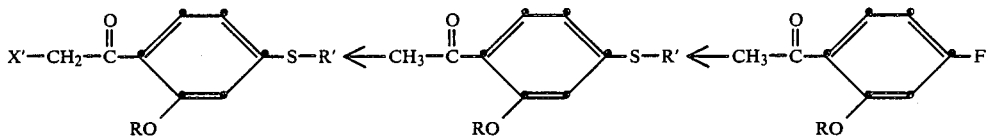

III' (n = 0)

Following the procedure of Scheme II, commercially available 3-fluorophenol is acetylated and then subjected to a Fries Rearrangement to provide 4-fluoro-2-hydroxyacetophenone. The phenol is then alkylated and the $C_1$–$C_4$ alkylmercapto functionality is introduced by displacing the fluorine substituent with the appropriate R' mercaptan anion. The α-halo substituent is introduced in the same manner as previously described. The oxidation of the thioether is performed, if desired, in the usual way either on the α-halo-acetophenone III' or the non-halogenated precursor.

In addition, some of the compounds of Formula I may be prepared by subsequent derivatizations of other compounds of Formula I by methods known in the art. Thus, mercapto derivatives of Formula I may be transformed into the respective sulfinyl and sulfonyl compounds, amine derivatives may be prepared from intermediate halo derivatives, phenol substituents may be selectively alkylated, and like transformations.

Illustrative of the compounds of this invention are the following:

2-[2-(β-methylsulfinylethoxy)-4-methoxyphenyl]imidazo[1,2-a]pyrazine,
7-(2-methoxy-4-methylsulfonylphenyl)imidazo[1,2-a]-1,3,5-triazine,
2-[2-methoxy-4-(γ-methylmercaptopropoxy)phenyl]imidazo[1,2-c]pyrimidine,
6-[2-methoxy-4-(β-ethylsulfinylethoxy)phenyl]imidazo[1,2-b][1,2,4]triazine,
7-(2-butoxy-4-methylphenyl)imidazo[2,1-c][1,2,4]triazine,
6-[2-(γ-methylsulfinylpropoxy)-4-methoxyphenyl]imidazo[1,2-b][1,2,4]triazine,
6-[2-(β-methylsulfinylethoxy)phenyl]imidazo[2,1-f][1,2,4]triazine,
2-(2-methoxy-4-methylphenyl)imidazo[1,2-d][1,2,4]triazine,
2-(2-methoxy-4-methylsulfinylphenyl)imidazo[1,2-a]pyrimidine,
7-[2-(β-methylmercaptoethoxy)-5-methylmercaptophenyl]imidazo[1,2-a]-1,3,5-triazine,
2-[2-(β-ethylsulfinylethoxy)-4-methoxyphenyl]imidazo[1,2-a]pyrazine,
6-(2-methoxy-4-hydroxyphenyl)imidazo[1,2-c][1,2,3]triazine,
2-(2,4-dimethoxyphenyl)imidazo[1,2-c]pyrimidine,
2-(2,4-dimethoxyphenyl)imidazo[1,2-a]pyrimidine,
6-(2-methoxy-4-methylmercaptophenyl)imidazo[1,2-c][1,2,3]triazine,
7-(2-methoxy-4-methylsulfinylphenyl)imidazo[2,1-c][1,2,4]triazine,
2-(2-methoxy-4-methylsulfonylphenyl)imidazo[1,2-d][1,2,4]triazine,
6-(2-methoxy-4-methylsulfinylphenyl)imidazo[2,1-f][1,2,4]triazine,
2-(2,4,5-trimethoxyphenyl)imidazo[1,2-a]pyrazine,
6-[2-(β-methylsulfinylethoxy)-4-methylphenyl]imidazo[1,2-b][1,2,4]triazine,
7-[2-methoxy-4-(β-methylmercaptoethoxy)phenyl]imidazo[1,2-a]-1,3,5-triazine,
2-(2,4-dimethoxyphenyl)imidazo[1,2-d][1,2,4]triazine,
2-(2-fluoro-5-methylsulfinylphenyl)imidazo[1,2-a]pyrazine,
6-(2,4-dimethoxyphenyl)imidazo[1,2-c][1,2,3]triazine,
7-(2-ethoxy-4-propylsulfinylphenyl)imidazo[1,2-a]-1,3,5-triazine,
6-[2-(β-methoxyethoxy)-4-methoxyphenyl]imidazo[1,2-c][1,2,3]triazine,
2-(2-ethoxy-4-ethylsulfonylphenyl)imidazo[1,2-d][1,2,4]triazine,
2-(4-isopropoxyphenyl)imidazo[1,2-a]pyrazine,
6-(2-β-phenylsulfinylethoxy-4-methoxyphenyl)imidazo[2,1-f][1,2,4]triazine,
7-[2-(β-methylmercaptoethoxy)-4-methylmercaptophenyl]imidazo[1,2-a]-1,3,5-triazine,
2-(2-methylmercaptophenyl)imidazo[1,2-c]pyrimidine,
7-[2,4-bis(methylmercapto)phenyl]imidazo[2,1-c][1,2,4]triazine,
2-(2,4-diethoxyphenyl)imidazo[1,2-a]pyrimidine,
2-(2-methoxy-4-methylmercaptophenyl)imidazo[1,2-d][1,2,4]triazine,
2-(2-methoxy-4-methylsulfonylphenyl)imidazo[1,2-c]pyrimidine,
7-(2-methoxy-4-methylsulfinylphenyl)imidazo[1,2-a]-1,3,5-triazine,
6-(2,4-dimethoxyphenyl)imidazo[2,1-f][1,2,4]-triazine,
7-[2-(β-ethylmercaptoethoxy)-4-methoxyphenyl]imidazo[2,1-c][1,2,4]triazine,
6-(2-methoxy-4-propylsulfonylphenyl)imidazo[1,2-b][1,2,4]triazine,
2-(2-ethoxy-5-methylsulfinylphenyl)imidazo[1,2-c]pyrimidine,
2-(4-aminophenyl)imidazo[1,2-a]pyrazine,
7-(2,4-dimethoxyphenyl)imidazo[2,1-c][1,2,4]triazine,
2-(2-ethoxy-4-ethylsulfinylphenyl)imidazo[1,2-c]pyrimidine,
6-(2,4,6-trimethoxyphenyl)imidazo[2,1-f][1,2,4]triazine,
2-(2-ethoxy-4-butylsulfinylphenyl)imidazo[1,2-c]pyrimidine,
2-(2-methoxy-4-methylsulfinylphenyl)imidazo[1,2-a]pyrimidine,
2-(3-methoxy-4-hydroxyphenyl)imidazo[1,2-c]pyrimidine,
6-(2,6-dichlorophenyl)imidazo[1,2-c][1,2,3]triazine,
7-(2-ethoxy-4-butylsulfonylphenyl)imidazo[1,2-a]-1,3,5-triazine,
2-[2-β-(4-hydroxyphenylsulfinyl)ethoxy-4-methoxyphenyl]imidazo[1,2-d][1,2,4]triazine,
2-(2-fluoro-4-methoxyphenyl)imidazo[1,2-a]pyrazine,
2-(2-methylaminophenyl)imidazo[1,2-c]pyrimidine,
2-(4-methylmercaptophenyl)imidazo[1,2-c]pyrimidine, 2-(2-methoxy-4-methylsulfonylphenyl)imidazo[1,2-a]pyrazine,
6-(2-methoxy-4-methylsulfonylphenyl)imidazo[1,2-b][1,2,4]triazine,
6-(2-methoxy-4-methylmercaptophenyl)imidazo[2,1-f][1,2,4]triazine,
2-(2-allyloxy-4-methoxyphenyl)imidazo[1,2-a]pyrazine,
6-[2-methoxy-4-(β-ethylmercaptoethoxy)phenyl]imidazo[1,2-c][1,2,3]triazine,
6-(2,4-dimethoxyphenyl)imidazo[1,2-b][1,2,4]triazine,
7-(2-methoxyphenyl)imidazo[1,2-a]-1,3,5-triazine,
7-(2-fluoro-4-methylsulfinylphenyl)imidazo[1,2-a]-1,3,5-triazine,
6-(3-butyl-4-methoxyphenyl)imidazo[1,2-b][1,2,4]triazine,
2-(3,4-dimethoxyphenyl)imidazo[1,2-c]pyrimidine,
2-(2-chlorophenyl)imidazo[1,2-d][1,2,4]triazine,
2-(2-ethoxy-4-butylmercaptophenyl)imidazo[1,2-c]pyrimidine,
6-(2-fluoro-5-methylmercaptophenyl)imidazo[2,1-f][1,2,4]triazine
2-(4-hydroxyphenyl)imidazo[1,2-a]pyrazine,
2-(2-ethoxy-4-methylphenyl)imidazo[1,2-a]pyrazine,
2-(4-methoxyphenyl)imidazo[1,2-c]pyrimidine,
7-[2-methoxy-4-(β-methylsulfinylethoxy)phenyl]imidazo[2,1-c][1,2,4]triazine,
2-[2-γ-(3,4-dichlorophenoxy)propoxyphenyl]imidazo[1,2-a]pyrazine,
2-[2-(β-methylsulfinylethoxy)-4-methylmercaptophenyl]imidazo[1,2-c]pyrimidine,
7-(2,4-dimethoxy-3-hydroxyphenyl)imidazo[1,2-a]-1,3,5-triazine,
2-(2-methoxy-4-methylmercaptophenyl)imidazo[1,2-c]pyrimidine,
6-(2-methoxy-4-methylsulfonylphenyl)imidazo[1,2-c][1,2,3]triazine,
2-(2,4-dimethoxyphenyl)imidazo[1,2-a]pyrazine,
2-(2-methoxy-4-methylsulfinylphenyl)imidazo[1,2-c]pyrimidine,
2-(2-hydroxy-4-methoxyphenyl)imidazo[1,2-c]pyrimidine,
6-(2-ethoxy-4-propylmercaptophenyl)imidazo[1,2-b][1,2,4]triazine,
2-(2-fluoro-5-methylsulfonylphenyl)imidazo[1,2-a]pyrazine,
6-(2-methoxy-4-butylmercaptophenyl)imidazo[1,2-c][1,2,3]triazine,
6-[2-(γ-ethylsulfinylpropoxy)-4-methoxyphenyl]imidazo[1,2-b][1,2,4]triazine,
6-[2-(β-methylsulfinylethoxy)-4-methylsulfinylphenyl]imidazo[1,2-b][1,2,4]triazine,
7-(2-methoxy-4-propylsulfinylphenyl)imidazo[1,2-a]-1,3,5-triazine,
2-(3,5-dimethoxyphenyl)imidazo[1,2-d][1,2,4]triazine,
2-[2-(β-methylmercaptoethoxy)-4-methoxyphenyl]imidazo[1,2-c]pyrimidine,
2-(2,6-dimethoxyphenyl)imidazo[1,2-a]pyrimidine,
6-(2-methoxy-4-ethoxyphenyl)imidazo[2,1-f][1,2,4]triazine,
2-(2-methoxy-4-dimethylaminophenyl)imidazo[1,2-c]pyrimidine,
6-(4-nitro-2-hydroxyphenyl)imidazo[1,2-b][1,2,4]triazine,
2-(3-cyanophenyl)imidazo[1,2-c]pyrimidine,
2-(4-isopropylphenyl)imidazo[1,2-a]pyrazine,
7-(2-β-phenylethoxyphenyl)imidazo[2,1-c][1,2,4]triazine,
7-(2,4-dimethoxyphenyl)imidazo[1,2-a]-1,3,5-triazine, 6-(2-methoxy-4-methylsulfinylphenyl)imidazo[1,2-c][1,2,3]triazine,
6-(2-methoxy-4-methylsulfonylphenyl)imidazo[1,2-b][1,2,4]triazine,
7-(2-methoxy-4-methylmercaptophenyl)imidazo[2,1-c][1,2,4]triazine,
7-(2,4-dihydroxyphenyl)imidazo[2,1-c][1,2,4]triazine,
2-(2-methoxy-4-methylsulfonylphenyl)imidazo[1,2-a]pyrimidine,
2-(2-methoxy-4-propylmercaptophenyl)imidazo[1,2-c]pyrimidine,
6-[2-methoxy-4-(γ-ethylsulfinylpropoxy)phenyl]imidazo[2,1-f][1,2,4]triazine,
2-(2-methoxy-4-chlorophenyl)imidazo[1,2-d][1,2,4]triazine,
2-[2-(γ-ethylmercaptopropoxy)-4-methoxyphenyl]imidazo[1,2-a]pyrazine,
2-(4-methylsulfonylphenyl)imidazo[1,2-c]pyrimidine,
2-(2-hexyloxy-4-methylphenyl)imidazo[1,2-a]pyrimidine,
2-(2-octyloxy-4-methoxyphenyl)imidazo[1,2-c]pyrimidine,
2-(2-methoxy-4-ethylmercaptophenyl)imidazo[1,2-a]pyrazine,
6-(4-dimethylaminophenyl)imidazo[1,2-b][1,2,4]triazine,
2-[2-methoxy-4-(γ-ethylmercaptopropoxy)phenyl]imidazo[1,2-a]pyrimidine,
6-(2,4-dimethylphenyl)imidazo[1,2-c][1,2,3]triazine,
7-(2-methylsulfinylphenyl)imidazo[1,2-a]1,3,5-triazine,
2-[2-(β-methylsulfinylethoxy)mercaptophenyl]imidazo[1,2-c]pyrimidine,
7-(2-methoxy-4-methylmercaptophenyl)imidazo[1,2-a]-1,3,5-triazine,
6-(2-methoxy-4-methylsulfonylphenyl)imidazo[2,1-f][1,2,4]triazine,
2-(2-methoxy-4-methylsulfinylphenyl)imidazo[1,2-d][1,2,4]triazine,
2-(3,4-dimethoxyphenyl)imidazo[1,2-a]pyrimidine,
2-(2-methoxy-4-methylmercaptophenyl)imidazo[1,2-a]pyrazine,
2-(2,3,4-trimethoxyphenyl)imidazo[1,2-c]pyrimidine,
6-(3,4,5-trimethoxyphenyl)imidazo[1,2-c][1,2,3]triazine,
7-(2-methoxy-4-ethylsulfinylphenyl)imidazo[1,2-a]-1,3,5-triazine,
2-[2-(β-methylsulfinylethoxy)phenyl]imidazo[1,2-d][1,2,4]triazine,
2-[2-(γ-methylmercaptopropoxy)-4-methoxyphenyl]imidazo[1,2-c]pyrimidine,
6-(4-iodophenyl)imidazo[2,1-f][1,2,4]triazine,
2-[2-methoxy-4-(β-butylsulfinylethoxy)phenyl]imidazo[1,2-a]pyrazine,
6-[2-(β-methoxyethoxy)phenyl]imidazo[1,2-b][1,2,4]triazine,
2-(2-fluorophenyl)imidazo[1,2-c]pyrimidine,
2-(3-isopropoxyphenyl)imidazo[1,2-a]pyrazine,
2-(2-ethoxy-4-ethylmercaptophenyl)imidazo[1,2-c]pyrimidine,
7-(4-fluoro-2-methoxyphenyl)imidazo[2,1-c][1,2,4]triazine,
2-(2-methoxy-4-methylmercaptophenyl)imidazo[1,2-a]pyrimidine,
7-(2-fluoro-4-methylmercaptophenyl)imidazo[1,2-a]-1,3,5-triazine,
7-(2-methoxy-4-methylsulfonylphenyl)imidazo[2,1-c][1,2,4]triazine,
6-(2-methoxy-4-methylmercaptophenyl)imidazo[1,2-b][1,2,4]triazine, 7-[2-methoxy-4-(γ-methylsulfinylpropoxy)phenyl]imidazo[1,2-a]-1,3,5-triazine, 2-(2-methylsulfonylphenyl)imidazo[1,2-a]pyrimidine, 2-(4-butoxyphenyl)imidazo[1,2-c]pyrimidine, 6-(4-methylsulfinylphenyl)imidazo[1,2-c][1,2,3]triazine, and 2-(2-methoxy-4-benzyloxyphenyl)imidazo[1,2-a]pyrazine.

The pharmaceutically acceptable acid addition salts of this invention include salts derived from inorganic acids such as: hydrochloric acid, nitric acid, phosphoric acid, sulfuric acid, hydrobromic acid, hydroiodic acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially the hydrochloride and hydrobromide salt forms.

The compounds may be administered by various routes including the oral, rectal, transdermal, subcutaneous, intravenous, intramuscular, or intranasal routes, being usually employed in the form of a pharmaceutical composition, although it is a special feature of these compounds that they are effective positive inotropic agents following oral administration. Such compositions are prepared in a manner well known in the pharmaceutical art and comprise at least one active compound. Accordingly the invention includes a pharmaceutical composition comprising as active ingredient a compound of Formula I or an acid addition salt thereof, associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle excipient or medium for the active ingredient. Thus the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injection solutions and sterile packaged powders.

Some examples of suitable carriers are lactose, dextrose, sucrose, sorbitol, mannitol, starches, gum acacia, calcium phosphate, alginates, tragecanth, gelatin, calcium silicate, microcrystalline cellulose, polyvinylpyrrolidone, cellulose, water, syrup, methyl cellulose, methyl- and propyl-hydroxygenzoates, talc, magnesium stearate or mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

Preferably the compositions are formulated in a unit dosage form, each dosage containing from 5 to 500 mg., more usually 25 to 300 mg., of the active ingredient. The term "unit dosage form" refers to physically discrete units suitable as unitary dosages for human subjects and animals, each unit containing a predetermined quantity of active material calculated to produce the desired therapeutic effect, in association with the required pharmaceutical carrier.

The active compounds are effective over a wide dosage range. For example, dosages per day will normally fall within the range of 0.5 to 300 mg./kg. In the treatment of adult humans, the range of about 1 to 50 mg./kg., in single or divided doses, is preferred. However it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

In an effort to more fully illustrate this invention, the following detailed preparations and examples are provided. The examples are illustrative only and are not intended to limit the scope of the invention. The term "m/e" used in characterizing the products refers to the mass-to-charge ratio of ions which appear in the mass spectra of the products. In general, the values correspond to molecular weights of the major peaks, and are so designated "M+".

PREPARATION 1

α-bromo-2,4-dimethoxyacetophenone

Fifty-three grams of aluminum chloride were added in portions to 55.2 ml. (400 mmoles) of 1,3-dimethoxybenzene and 34.5 ml. (400 mmoles) of bromoacetyl bromide using an external ice-bath to keep the temperature around 0° C. After the aluminum chloride addition was complete, the ice-bath was removed and the reaction mixture was allowed to stir for 2 hours. The reaction mixture was carefully added to ice water and the resulting mixture extracted with 1500 ml. of ethyl acetate. The organic phase was washed with 500 ml. of 1N hydrochloric acid. The organic phase was separated, dried, and evaporated in vacuo. The residue was crystallized from diethyl ether to give 54.1 g. of the title product as a white crystalline solid.

PREPARATION 2

α-bromo-2-methoxy-4-methylmercaptoacetophenone

A. Preparation of 2-hydroxy-4-benzyloxyacetophenone

Fifty grams of 2,4-dihydroxyacetophenone were dissolved in 250 ml. of dimethylformamide and the solution was cooled to 0° C. by means of an external ice-bath. After the addition of 15 grams of a 50% oil dispersion of sodium hydride, 40 ml. of benzyl chloride were added in a dropwise fashion and the reaction was allowed to warm to room temperature. After stirring overnight, the reaction mixture was added to 700 ml. of ethyl acetate. The organic phase was washed with 1000 ml. of 1N hydrochloric acid and twice each with 1000 ml. of a saturated sodium chloride solution. The organic layer was dried, and the solvent removed in vacuo. The oily residue was treated with 100 ml. of methanol and 50 ml. of hexane. The desired 2-hydroxy-4-benzyloxyacetophenone (36.7 grams) was recovered by filtration.

B. Preparation of 2-methoxy-4-benzyloxyacetophenone

Seventy grams of 2-hydroxy-4-benzyloxyacetophenone were dissolved in 300 ml. of dimethylformamide and the solution cooled to 0° C. by means of an external ice-bath. After the addition of 13.2 grams of a 50% oil dispersion of sodium hydride, 54 ml. of methyl iodide were added to the reaction mixture. The reaction mixture was then allowed to warm to room temperature and stirred overnight. The reaction mixture was then added to 500 ml. of ethyl acetate and washed three times each with 500 ml. of a saturated sodium chloride solution. The organic phase was dried and the solvent removed in vacuo. Hexane was added and 52 grams of crystalline 2-methoxy-4-benzyloxyacetophenone were recovered by filtration.

C. Preparation of 2-methoxy-4-hydroxyacetophenone

Twenty grams of 5% palladium-on-carbon were added to a solution of 94.6 grams of 2-methoxy-4-benzyloxyacetophenone in 785 ml. of tetrahydrofuran. The mixture was hydrogenated at 45°-50° C. for five hours at 60 psi, at which point 95% of the theoretical hydrogen uptake had occurred. The catalyst was removed by filtration and the solvent removed in vacuo. Fifty-two grams of 2-methoxy-4-hydroxyacetophenone were recovered as a solid. The product was used in the subsequent step without further purification.

D. Preparation of 2-methoxy-4-(dimethylthiocarbamoyloxy)-acetophenone

To a suspension of 7.5 grams of a 50% oil dispersion of sodium hydride in 75 ml. of dimethylformamide were added 26.5 grams of 2-methoxy-4-hydroxyacetophenone with the reaction mixture cooled by means of an external ice-bath. After the addition of 23.2 grams of dimethylthiocarbamoyl chloride, the reaction mixture was stirred overnight at room temperature. The reaction mixture was poured into 500 ml. of ethyl acetate and washed with 300 ml. of a saturated sodium chloride solution. The aqueous layer was extracted with 300 ml. of ethyl acetate and the combined ethyl acetate solutions were washed three times each with 500 ml. of a saturated sodium chloride solution. The organic layer was dried and the solvent removed in vacuo. The residual oil was triturated with hexane. The hexane was decanted and a small volume of diethyl ether was added causing crystallization to occur. Upon filtration, 15.4 grams of the desired 2-methoxy-4-(dimethylthiocarbamoyloxy)-acetophenone were recovered from the ether mixture plus an additional 3.5 grams which crystallized from the decanted hexane.

E. Preparation of 2-methoxy-4-(dimethylcarbamoylmercapto)-acetophenone

Ten grams of 2-methoxy-4-(dimethylthiocarbamoyloxy)-acetophenone were placed into each of two 100 ml. flasks under a nitrogen blanket and were heated to 235°-240° C. in an oil-bath for one hour. The resulting residues were combined and purified by column chromatography over silica gel eluting with 50% ethyl acetate/hexane. The product was collected and crystallized from a minimum volume of ether to give 8.3 grams of 2-methoxy-4-(dimethylcarbamoylmercapto)-acetophenone.

F. Preparation of 2-methoxy-4-mercaptoacetophenone

A solution of 1.8 grams of 2-methoxy-4-(dimethylcarbamoylmercapto)-acetophenone in 20 ml. of methanol and 7.2 ml. of 5N sodium hydroxide was allowed to reflux for two hours. The reaction mixture was then poured into 200 ml. of ethyl acetate. After washing with 200 ml. of 1N hydrochloric acid, the organic phase was dried and evaporated in vacuo. The residue crystallized on removal of the solvent to give 1.1 grams of 2-methoxy-4-mercaptoacetophenone.

Analysis: $C_9H_{10}O_2S$; Calc: C, 59.32; H, 5.53; S, 17.59; Found: C, 59.70; H, 5.55; S, 17.41.

G. Preparation of 2-methoxy-4-methylmercaptoacetophenone

Three grams of 2-methoxyl-4-mercaptoacetophenone were dissolved in 30 ml. of methanol. Three grams of potassium hydroxide were added, followed by the addition of 3 ml. of methyl iodide. The reaction was stirred for 30 minutes at room temperature. The reaction mixture was poured into 200 ml. of ethyl acetate, washed with 200 ml. of a saturated sodium chloride solution, dried, and evaporated in vacuo. The residual oil was dissolved in a small volume of ether and hexane was added until cloudy. Crystallization ensued giving 2.3 grams of 2-methoxy-4-methylmercaptoacetophenone.

Analysis: $C_{10}H_{12}O_2S$; Calc.: C, 61.20; H, 6.16; S, 16.34; Found: C, 61.45; H, 5.91; S, 16.63.

H. Preparation of α-bromo-2-methoxy-4-methylmercaptoacetophenone

A solution of 1.6 ml. of diisopropylamine in 30 ml. of dry tetrahydrofuran was cooled to −20° C. under a nitrogen atmosphere. Seven ml. of a 1.6M solution of n-butyllithium were slowly added to the solution. The solution was stirred for 20 minutes keeping the temperature between −5° and −20° C. The temperature was then lowered to −78° C. and a solution of 2 grams of 2-methoxy-4-methylmercaptoacetophenone in 10 ml. of dry tetrahydrofuran was introduced. After stirring the solution at −78° C. for 30 minutes, 2 ml. of chlorotrimethylsilane were added. The solution was brought to room temperature and stirred for 90 minutes. The solvent was removed in vacuo and 200 ml. of diethyl ether were added to the residue. The solution was filtered and the filtrate was evaporated in vacuo affording 2.3 grams of a solid. The solid was dissolved in 35 ml. of dry tetrahydrofuran under a nitrogen atmosphere. The solution was cooled to 0° C. and 1.8 grams of N-bromosuccinimide were added. After stirring for 45 minutes at 0° C., 200 ml. of methylene chloride were added to the solution. The solution was washed with a cold solution of sodium bicarbonate. The organic layer was separated, dried over magnesium sulfate, and evaporated in vacuo. The resulting residue was crystallized from diethyl ether affording 1.05 grams of α-bromo-2-methoxy-4-methylmercaptoacetophenone, M+=274, 276. The proton NMR spectrum was consistent with the structure.

PREPARATION 3

α-bromo-2-methoxy-4-methylsulfinylacetophenone

A solution of 1.5 grams of α-bromo-2-methoxy-4-methylmercaptoacetophenone in 75 ml. of methylene chloride was cooled to 0° C. after which one equivalent (760 mg.) of 85% meta-chloroperbenzoic acid was introduced. After one hour of stirring at 0° C., 200 ml. of methylene chloride were added and the organic solution was washed with a cold sodium bicarbonate solution. The organic layer was dried over magnesium sulfate and the solvent was removed in vacuo. The oily residue could be used without further purification for the subsequent reactions. Crystallization from ether provided the purified title product, M+=290, 292.

Analysis: $C_{10}H_{11}BrSO_3$; Calc.: C, 41.25; H, 3.81; S, 11.01; Br, 27.44; Found: C, 40.76; H, 3.82; S, 10.40; Br, 28.58.

PREPARATION 4

α-bromo-2-methoxy-4-methylsulfonylacetophenone

A. Preparation of 3-fluorophenylacetate

To a solution of 20 ml. of 3-fluorophenol in 200 ml. of dry methylene chloride were added 19.5 ml. of pyridine. The solution was cooled to 0° C. and 17.5 ml. of acetyl chloride were added dropwise with stirring. After the addition was complete, the reaction was stirred for 1 hour at 0° C. An additional 200 ml. of methylene chloride was added and the organic solution was extracted once with 300 ml. of 1N hydrochloric acid. The organic solution was dried with magnesium sulfate and removed in vacuo to give 34.3 g. of 3-fluorophenylacetate as an oil which was used in the subsequent step without further purification.

B. Preparation of 2-hydroxy-4-fluoroacetophenone

To a flask containing 34.2 g. of 3-fluorophenylacetate which was cooled to 0° C. were added 40 g. of aluminum chloride in portions. The flask and its contents were allowed to warm to room temperature and the reaction was then placed in an oil bath and heated to 160°–180° C. for 2 hours. The reaction was then cooled to 0° C. and ice was carefully added followed by the addition of 150 ml. of concentrated hydrochloric acid and 250 ml. of ethyl acetate. The mixture was then allowed to stir until a complete solution occurred. The layers were separated and the ethyl acetate was removed in vacuo. The residue was subjected to steam distillation. The distillate was acidified with 1N hydrochloric acid and extracted with ethyl acetate. The ethyl acetate layer was dried and the solid was removed in vacuo to give 28 g. of 2-hydroxy-4-fluoroacetophenone as an oil which crystallized on cooling.

C. Preparation of 2-methoxy-4-fluoroacetophenone

To a solution of 13.9 g. of 2-hydroxy-4-fluoroacetophenone and 75 ml. of dried dimethylformamide were added 30 ml. of methyl iodide. The solution was cooled to 0° C. and 4.1 g. of a 50% oil dispersion of sodium hydride were carefully added. After stirring for 1 hour at 0° C., the reaction was extracted with ethyl acetate. The organic extract was washed three times with 200 ml. each of 1N hydrochloric acid. The ethyl acetate solution was then dried and removed in vacuo. This reaction and a subsequent identical reaction provided a total of 28 g. of 2-methoxy-4-fluoroacetophenone as an oil which was used in the subsequent step without further purification.

D. Preparation of 2-methoxy-4-methylmercaptoacetophenone

A suspension of 17 g. of potassium hydroxide in 100 ml. of dry dimethylformamide under a nitrogen atmosphere was cooled to −10° C. with an external ice/acetone bath. To this suspension were added 26 ml. of methanethiol. The reaction mixture was stirred until all the potassium hydroxide was dissolved. At this time, 33.1 g. of 2-methoxy-4-fluoroacetophenone were added and the reaction mixture was stirred for 2 hours at 0° C. The reaction mixture was poured into 400 ml. of ethyl acetate and the resulting solution was washed three times each with 300 ml. of 1N hydrochloric acid. The organic phase was then dried and evaporated in vacuo to give an oil. Crystallization from 50% ether/hexane afforded 21.3 g. of the desired 2-methoxy-4-methylmercaptoacetophenone.

E. Preparation of 2-methoxy-4-methylsulfonylacetophenone

To a solution of 3.92 g. of 2-methoxy-4-methylmercaptoacetophenone in 200 ml. of methylene chloride were added 4 g. of m-chloroperbenzoic acid. Thin-layer chromatography indicated the formation of the intermediate sulfoxide derivative. This was followed ten minutes later with a second addition of 4 g. of m-chloroperbenzoic acid. After stirring for one hour, the reaction mixture was washed with 500 ml. of a saturated sodium bicarbonate solution. The organic phase was separated and dried over magnesium sulfate. The organic solution was then evaporated in vacuo to give 3.61 g. of 2-methoxy-4-methylsulfonylacetophenone.

F. Preparation of α-bromo-2-methoxy-4-methylsulfonylacetophenone

To a suspension of 3.61 g. of 2-methoxy-4-methylsulfonylacetophenone and 100 ml. of acetic acid was added enough methylene chloride to cause solution. While stirring at room temperature, 0.91 ml. of bromine were added. The reaction was stirred until the bromine color was discharged. The reaction was poured into 300 ml. of ethyl acetate and washed twice each with 300 ml. of a saturated sodium chloride solution. The organic solution was further washed with 300 ml. of a saturated sodium bicarbonate solution. The organic phase was dried and the solvent was removed in vacuo. The residual oil crystallized on the addition of diethyl ether giving 4.05 g. of the desired α-bromo-2-methoxy-4-methylsulfonylacetophenone.

Analysis: $C_{10}H_{11}BrSO_4$; Calc.: C, 39.10; H, 3.61; S, 10.44; Br, 26.01; Found: C, 38.92; H, 3.51; S, 10.28; Br, 26.30.

EXAMPLE 1

2-(2,4-dimethoxyphenyl)imidazo[1,2-a]pyrimidine

A solution of 1.9 g. (20 mmoles) of 2-aminopyrimidine and 5.2 g. of α-bromo-2,4-dimethoxyacetophenone in 40 ml. of dimethylformamide was stirred at room temperature for about 60 hours. The reaction mixture was poured into approximately 300 ml. of ethyl acetate. The organic solution was then washed with a saturated sodium bicarbonate solution followed by two washes with 300 ml. each of saturated sodium chloride solution. The organic phase was dried, and the solvent was removed in vacuo. The resulting residue was crystallized from hot ethanol to give 2 g. of the title product, M+ = 255.

Analysis: $C_{14}H_{13}N_3O_2$; Calc.: C, 65.87; H, 5.13; N, 16.46; Found: C, 65.59; H, 5.08; N, 16.30.

EXAMPLE 2

2-(2,4-dimethoxyphenyl)imidazo[1,2-a]pyrimidine hydrobromide

A solution of 5.7 g. of 2-aminopyrimidine and 15.6 g. of α-bromo-2,4-dimethoxyacetophenone in 30 ml. of dimethylformamide was stirred at room temperature for 4 hours. The resulting precipitate was collected by filtration and washed with ethyl acetate to give 10 g. of the title product, M+ = 255.

Analysis: $C_{14}H_{13}N_3O_2.HBr$; Calc.: C, 50.02; H, 4.20; N, 12.50; Found: C, 49.82; H, 4.07; N, 12.30.

EXAMPLE 3

2-(2,4-dimethoxyphenyl)imidazo[1,2-a]pyrazine

Following the procedure of Example 1, 1.9 g. of 2-aminopyrazine and 5.2 g. of α-bromo-2,4-dimethoxyacetophenone were reacted in 40 ml. of dimethylformamide. The product was purified by chromatography over silica gel eluting with 10% methanol in ethyl acetate to give 330 mg. of the title product, M+ = 255.

Analysis: $C_{14}H_{13}N_3O_2$; Calc.: C, 65.87; H, 5.13; N, 16.46; Found: C, 63.39; H, 5.66; N, 15.46.

EXAMPLE 4

6-(2,4-dimethoxyphenyl)imidazo[1,2-b][1,2,4]triazine

Following the procedure of Example 1, 1.9 g. of 3-amino-1,2,4-triazine and 2.7 g. of α-bromo-2,4-dimethoxyacetophenone were heated for 2 hours at 60° C. in 30 ml. of dimethylformamide. The reaction mixture was added to 300 ml. of ethyl acetate and washed with 300 ml. of saturated sodium bicarbonate solution followed by two washings each with 300 ml. of saturated sodium chloride. The organic layer was evaporated to dryness and the residue purified by chromatography over silica gel eluting with ethyl acetate to give 200 mg. of the title product, M+ = 256.

Analysis: $C_{13}H_{12}N_4O_2$; Calc.: C, 60.93; H, 4.72; N, 21.86; Found: C, 60.57; H, 4.52; N, 21.56.

EXAMPLE 5

2-(2,4-dimethoxyphenyl)imidazo[1,2-c]pyrimidine

A. Preparation of 4-amino-6-chloropyrimidine

The preparation of the above starting material was carried out following the procedure in *J. Am. Chem. Soc.,* 76, 3225 (1954).

B. Preparation of 2-(2,4-dimethoxyphenyl)-6-chloro-imidazo[1,2-c]pyrimidine hydrobromide Following the procedure of Example 2, 2.6 g. (20 mmoles) of 4-amino-6-chloropyrimidine and 5.2 g. of α-bromo-2,4-dimethoxyacetophenone were stirred in 10 ml. of dimethylformamide for 3 days at room temperature. The resulting precipitate was filtered and washed with ethyl acetate to give 7.37 g. of the desired product, M+ = 289.

Analysis: $C_{14}H_{12}ClN_3O_2.HBr$; Calc.: C, 45.37; H, 3.54; N, 11.34; Cl, 9.57; Br, 21.56; Found: C, 45.08; H, 3.31; N, 11.14; Cl, 9.35; Br, 21.32.

C. Preparation of 2-(2,4-dimethoxyphenyl)imidazo[1,2-c]pyrimidine

Approximately 7.3 g. of 2-(2,4-dimethoxyphenyl)-6-chloro-imidazo[1,2-c]pyrimidine hydrobromide were converted to the free base by suspending in ethyl acetate, adding 20 ml. of propylene oxide, and shaking until solution had occurred. The ethyl acetate solution was washed with water, dried, and the solid removed in vacuo to give the free amine.

A solution of 3 g. of 2-(2,4-dimethoxyphenyl)-6-chloro-imidazo[1,2-c]pyrimidine (free base) in ethyl acetate was treated with 1 g. of 5% palladium-on-carbon and subjected to hydrogenation until hydrogen uptake ceased. Two grams of triethylamine were added and hydrogenation was continued. When hydrogen uptake ceased, the catalyst was removed by filtration, and the ethyl acetate solution was washed with 300 ml. of a saturated sodium chloride solution. The organic solution was evaporated in vacuo, and the resulting residue was crystallized from ethyl acetate/ether to give 1.2 g. of the title product, M+ = 255.

Analysis: $C_{14}H_{13}N_3O_2$; Calc.: C, 65.87; H, 5.13; N, 16.46; Found: C, 64.75; H, 4.91; N, 15.61.

EXAMPLE 6

2-(2-methoxy-4-methylsulfinylphenyl)imidazo[1,2-a]pyrimidine hydrobromide

Following the procedure of Example 2, 294 mg. of 2-aminopyrimidine and 900 mg. of α-bromo-2-methoxy-4-methylsulfinylacetophenone were dissolved in 5 ml. of dimethylformamide and stirred overnight at room temperature. The resulting precipitate was collected by filtration and washed with hexane to give approximately 300 mg. of the title product, M+ = 287.

Analysis: $C_{14}H_{13}N_3O_2S.HBr$; Calc.: C, 45.66; H, 3.83; N, 11.41; S, 8.69; Br, 21.70; Found: C, 45.39; H, 3.86; N, 11.67; S, 8.49; Br, 21.51.

EXAMPLE 7

2-(2-methoxy-4-methylsulfonylphenyl)imidazo[1,2-a]pyrimidine hydrobromide

Following the procedure of Example 2, 1.26 g. of 2-aminopyrimidine and 4.05 g. of α-bromo-2-methoxy-4-methylsulfonylacetophenone in 10 ml. of dimethylformamide were stirred at room temperature for 6 hours. Filtration of the reaction mixture and washing with ethyl acetate provided 2.22 g. of the title product. Stirring the filtrate an additional 16 hours provided another 1.4 g. of product.

Analysis: $C_{14}H_{13}N_3O_3S.HBr$; Calc.: C, 43.76; H, 3.67; N, 10.94; S, 8.34; Br, 20.79; Found: C, 43.92; H, 3.54; N, 11.08; S, 8.27; Br, 20.68.

EXAMPLE 8

2-(2-methoxy-4-methylsulfonylphenyl)imidazo[1,2-a]pyrazine

Following the general procedure of Example 5(B), 3.88 g. of 2-amino-3-chloropyrazine and 9.21 g. of α-bromo-2-methoxy-4-methylsulfonylacetophenone were reacted to give 4.8 g. of the intermediate 8-chloro-2-(2- methoxy-4-methylsulfonylphenyl)imidazo[1,2-a]pyrazine hydrobromide. The hydrobromide salt (3.6 g.) was hydrogenated in 195 ml. of dimethylformamide and 2.7 g. of triethylamine in the presence of 1 g. of 5% palladium-on-barium sulfate. After filtration, the solution was poured into 700 ml. of ethyl acetate, washed four times with a saturated sodium chloride solution and the solvent concentrated in vacuo. At a reduced volume crystallization occurred and 540 mg. of the title product were recovered by filtration.

Analysis: $C_{14}H_{13}N_3O_3S$; Calc.: C, 55.43; H, 4.32; N, 13.85; S, 10.57; Found: C, 53.91; H, 4.01; N, 13.52; S, 9.91.

EXAMPLE 9

2-(2-methoxy-4-methylsulfinylphenyl)imidazo[1,2-a]pyrimidine

Following the procedure of Example 1, 2.0 g of 2-aminopyrimidine and about 4.9 g. of α-bromo-2-methoxy-4-methylsulfinylacetophenone were allowed to react in dimethylformamide. The solvent was evaporated in vacuo and the residue was chromatographed over silica gel (eluting with 20% methanol in ethyl acetate). The appropriate fractions were combined and evaporated to give 1.3 g. of the title product which contained about 2% of residual silica gel, $M^+ = 287$.

Analysis: $C_{14}H_{13}N_3O_2S$; Calc: C, 58.52; H, 4.56; N, 14.62; S, 11.16; Found: C, 57.35; H, 4.35; N, 13.71; S, 10.61.

The following formulation examples may employ as active compounds any of the pharmaceutical compounds of the invention.

EXAMPLE 10

Hard gelatin capsules are prepared using the following ingredients:

|  | Quantity (mg./capsule) |
| --- | --- |
| Active compound | 250 |
| Starch dried | 200 |
| Magnesium stearate | 10 |

The above ingredients are mixed and filled into hard gelatin capsules in 460 mg. quantities.

EXAMPLE 11

A tablet formula is prepared using the ingredients below:

|  | Quantity (mg./tablet) |
| --- | --- |
| Active compound | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 12

An aerosol solution is prepared containing the following components:

|  | Weight % |
| --- | --- |
| Active ingredient | 0.25 |
| Ethanol | 29.75 |
| Propellant 22 (Chlorodifluoromethane) | 70 |

The active compound is mixed with ethanol and the mixture added to a portion of the propellant 22, cooled to −30° C. and transferred to a filling device. The required amount is then fed to a stainless steel container and diluted further with the remainder of the propellant. The valve units are then fitted to the container.

EXAMPLE 13

Tablets each containing 60 mg. of active ingredient are made up as follows:

| Active ingredient | 60 mg. |
| --- | --- |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 14

Capsules each containing 80 mg. of medicament are made as follows:

| Active ingredient | 80 mg. |
| --- | --- |
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 15

Suppositories each containing 225 mg. of active ingredient are made as follows:

| Active ingredient | 225 mg. |
| --- | --- |
| Saturated fatty acid glycerides to | 2,000 mg. |

The active ingredient is passed through a No. 60 mesh U.S. sieve and suspended in the saturated fatty acid glycerides previously melted using the minimum heat necessary. The mixture is then poured into a suppository mold of nominal 2 g. capacity and allowed to cool.

EXAMPLE 16

Suspensions each containing 50 mg. of medicament per 5 ml. dose are made as follows:

| | |
|---|---|
| Active ingredient | 50 mg. |
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

The compounds of this invention and their pharmaceutically acceptable salts have been found to possess useful pharmaceutical properties, including positive inotropy and vasodilation. Certain compounds of the present invention were examined as to their pharmacodynamic effects in the following test systems.

POSITIVE INOTROPIC ACTIVITY IN ISOLATED CAT PAPILLARY MUSCLES

Cats of either sex were anesthetized with Metofane (1,1-difluoro-2,2-dichloroethyl methyl ether, Pittman-Moore) their hearts immediately removed and the papillary muscles dissected and suspended in individual organ baths. A platinum hook secured one end of the muscle to an electrode mounted in the bottom of the bath, and a silk thread attached the tendon to a Statham isometric transducer. The baths contained Krebs-Henseleit solution (36° C., bubbled with 95 percent oxygen-5 percent carbon dioxide) of the following millimolar composition: NaCl, 118; KCl, 4.5; CaCl$_2$, 2.5; KH$_2$PO$_4$, 1.1; MgSO$_4$, 1.2; NaHCO$_3$, 25; and glucose, 11.

A base-line tension of 1.5 g. was applied to each muscle. Square-wave pulses (5.0 msec. in duration, three times threshold voltage) delivered through the hook electrode and a second electrode positioned near the top of the muscle evoked 12 contractions/minute, which were recorded on a Grass polygraph. After the muscles had equilibrated for 60 minutes, the recorder gain was adjusted so that the pen deflected 10 mm. The drug was introduced in a solution of normal saline in an amount to bring the final concentration of the drug to $10^{-5}$ or $10^{-4}$ molar. Increases in contractility were tabulated as millimeters of pen deflection in excess of the baseline value. In each experiment the maximum contractility was measured. Test results are summarized in Table I and are expressed as percent of control (control=100 percent). Values are the average of results from 2 to 8 muscles.

TABLE I

Effects of Compounds of Formula I on Contractility in Cat Papillary Muscles

| Compound of Example No. | Contractility of Papillary Muscle* Drug Concentration | |
|---|---|---|
| | $10^{-5}$ M | $10^{-4}$ M |
| 1 | 131.0 | 140.0 |
| 2 | 113.0 | 130.0 |
| 3 | 153.5 | 242.0 |
| 4 | 118.0 | 244.5 |
| 5 | 117.0 | 157.3 |
| 7 | 126.5 | 164.5 |
| 9 | 115.0 | 145.0 |

*Data are peak responses at the indicated concentration of drug and are expressed as a percent of control (control = 100 percent).

EXPERIMENTS IN ANESTHETIZED DOGS

Mongrel dogs of either sex ranging in weight from 7 to 14 kg. were used. Anesthesia was induced with sodium pentobarbital (30 mg./kg., i.v.) and maintained with supplemental doses as required. A positive-pressure pump was used to ventilate the dogs through an endotracheal tube (18 strokes/minute, 20 ml./kg. stroke$^{-1}$), and a heating pad kept the body temperature at 37°-38° C.

Femoral arterial blood pressure was measured through a polyethylene catheter filled with heparin solution (16 units/ml.) and connected to a Statham pressure transducer. A strain-gauge arch sutured to the right ventricle of the heart measured cardiac contractility. Tension on the gauge was adjusted to 50 g. and the gain of the recorder (Beckman dynograph) was set so that 50 g. caused a 10-mm. pen deflection; cardiac contractile tension was measured as millimeters of pen deflection or grams of tension. The drug was administered following a 30–45 minute equilibrium period as an i.v. bolus (2-5 ml.) in a normal saline vehicle. In a control experiment, rapid intravenous injection of 50 ml. of 5 percent dextran and mechanical compression of the aorta showed that the contractility measurements were independent of changes in preload and afterload. Heart rate was derived by means of a cardiotach which was triggered by the arterial pressure pulse signal and displayed on the polygraph. The maximum effects on contractility at various dose levels are presented as a percent of control (control=100 percent) in Table II.

TABLE II

Effects of Compounds of Formula I on Ventricular Contractility in the Anesthetized Dog Effect on Contractility*

| Compound of Example No. | Drug Dose | | | |
|---|---|---|---|---|
| | 1 mg./kg. | 2 mg./kg. | 4 mg./kg. | 8 mg./kg. |
| 1 | 120 | 144 | 187 | 232 |
| 3 | 195 | 254 | 285 | 281 |
| 5 | 115 | 123 | NT** | NT |
| 8*** | NT | NT | NT | NT |
| 9 | 160 | 247 | 352 | 415 |

*Data are peak responses to an i.v. injection of drug and expressed as a percent of control (control = 100 percent).
**Not tested
***Compound 8 produced the following effects at the respective dose levels: 0.01 mg./kg.: 115%; 0.02 mg./kg.: 135%; 0.05 mg./kg.: 205%; 0.125 mg./kg.: 260%; 0.25 mg./kg.: 300%.

I claim:
1. Compounds of the formula

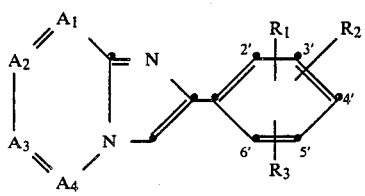

and their pharmaceutically acceptable salts, wherein two of $A_1$, $A_2$, $A_3$, and $A_4$ are N, and the remaining $A_1$, $A_2$, $A_3$, and $A_4$ are CH, and each of $R_1$, $R_2$, and $R_3$ is independently hydrogen, $C_1$-$C_4$ alkyl, $C_1$-$C_4$ alkoxy, allyloxy, benzyloxy, ($C_1$-$C_4$ alkyl)thio, ($C_1$-$C_4$ alkyl)sulfinyl, ($C_1$-$C_4$ alkyl)sulfonyl, hydroxy, halo, cyano, amino, mono- or di-($C_1$-$C_4$ alkyl)amino, trifluoromethyl, or Z-Q-substituted $C_1$-$C_4$ alkoxy, wherein Q is oxygen, sulfur, sulfinyl, sulfonyl, or a bond, and Z is $C_1$-$C_4$ alkyl, phenyl or phenyl substituted with halo $C_1$-$C_4$ alkyl, $C_1$-$C_4$ alkoxy, hydroxy, nitro, amino, $C_1$-$C_4$ alkylthio, $C_1$-$C_4$ alkylsulfinyl, or $C_1$-$C_4$ alkylsulfonyl, with the proviso that $R_1$, $R_2$, and $R_3$ may not all be hydrogen at the same time.

2. The compounds of claim 1 wherein $R_1$ is methoxy.

3. The compounds of claim 2 wherein $R_2$ is methylsulfinyl.

4. The compounds of claim 2 wherein $R_2$ is methoxy.

5. The compounds of claim 2 wherein $R_2$ is methylsulfonyl.

6. Th compounds of claim 1 which are 6-substituted-imidazo[1,2-b][1,2,4]triazines.

7. The compounds of claim 1 which are 7-substituted-imidazo[1,2-a]-1,3,5-triazines.

8. The compound of claim 6 which is 6-(2,4-dimethoxyphenyl)imidazo[1,2-b][1,2,4]triazine or a pharmaceutically acceptable salt thereof.

9. A method of producing a positive inotropic effect or causing vasodilation in a warm-blooded mammal, which comprises the administration to such mammal an effective amount of a compound of claim 1.

10. A pharmaceutical formulation useful for producing a positive inotropic effect or causing vasodilation in a mammal comprising from 5 to 500 mg of a compound of claim 1 in association with a pharmaceutically acceptable carrier or diluent.

* * * * *